United States Patent [19]

Chu et al.

[11] Patent Number: 4,681,933

[45] Date of Patent: Jul. 21, 1987

[54] 2',3'-DIDEOXY-5-SUBSTITUTED URIDINES AND RELATED COMPOUNDS AS ANTIVIRAL AGENTS

[75] Inventors: Chung K. Chu, Athens; Raymond F. Schinazi, Tucker, both of Ga.

[73] Assignees: University of Georgia Research Foundation, Inc., Athens; Emory University, Atlanta, both of Ga.

[21] Appl. No.: 857,947

[22] Filed: May 1, 1986

[51] Int. Cl.$^4$ .......................................... C07H 19/073
[52] U.S. Cl. ......................................... 536/23; 536/29
[58] Field of Search ............... 514/49, 50, 51; 536/23, 536/29

[56] References Cited

U.S. PATENT DOCUMENTS

| | | |
|---|---|---|
| 3,282,921 | 11/1966 | Verheyden et al. |
| 3,687,931 | 8/1972 | Verheyden et al. |
| 3,755,295 | 8/1973 | Verheyden et al. |
| 3,775,397 | 11/1973 | Etzold et al. |
| 3,817,982 | 6/1974 | Verheyden et al. |
| 4,128,639 | 12/1978 | Lin et al. ................................ 514/50 |
| 4,230,698 | 10/1980 | Bobek et al. |
| 4,331,662 | 5/1982 | Eckstein et al. |
| 4,604,382 | 8/1986 | Lin et al. .............................. 536/23 |

FOREIGN PATENT DOCUMENTS 0224490  7/1985  Fed. Rep. of Germany ........ 514/49

OTHER PUBLICATIONS

1-Pharmacology, vol. 97, 1982, p. 23.
Chemical Abstracts, vol. 96, 1982, p. 650.
Chemical Abstracts, vol. 98, 1983, pp. 428–429.
Chemical Abstracts, vol. 102, 1985, pp. 813–814.
J. Med. Chem., vol. 26, 1983, pp. 1691–1696, 544–548, 891–895.

Primary Examiner—Johnnie R. Brown
Attorney, Agent, or Firm—Oblon, Fisher, Spivak, McClelland & Maier

[57] ABSTRACT

A compound which exhibits antiviral activity towards HTLV-III/LAV, having the formula:

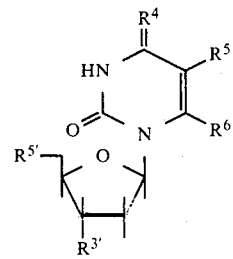

wherein $R^4$ is O or NH; $R^5$ is a $C_{2-4}$ alkyl group or a $C_{3-4}$ cycloalkyl group, wherein said alkyl group or cycloalkyl group may be substituted by one or more of Cl, Br, I, F, OH, $N_3$, $NH_2$, $SO_3H$, or COOH; $R^6$ is hydrogen or a $C_1$-$C_4$ alkyl group, which may be substituted by Cl, Br, I, F, OH, $N_3$, $NH_2$, $SO_3H$, or COOH; $R^{3'}$ is $N_3$, $NH_2$, or H; and $R^{5'}$ is $N_3$, $NH_2$, OH, phosphate, or a $C_{1-4}$ acyl group.

6 Claims, 2 Drawing Figures

2',3'-DIDEOXY-5-SUBSTITUTED URIDINES AND RELATED COMPOUNDS AS ANTIVIRAL AGENTS

The U.S. Government has rights in this invention as a result of the investigations leading to this invention being funded in part by a VA Merit Review Award.

BACKGROUND OF THE INVENTION

Field of the Invention

The present invention relates to certain 2',3'-dideoxy-5-substituted uridines and related compounds as agents for prevention and treatment of viral diseases, particularly HTLV-III/LAV, which causes acquired immunodeficiency syndrome (AIDS). The invention is also directed to a method of treatment of AIDS which involves treating the person afflicted with the disease with a composition including one or more of the compounds of the present invention.

Brief Description of the Background

AIDS was recognized as early as 1979. The number of cases reported to the Centers for Disease Control (CDC) increased dramatically each year since then, and in 1982 the CDC declared AIDS a new epidemic. Over 3,000 new cases were reported in 1984 alone. There are now close to 20,000 reported cases of AIDS, and approximately one half of those who have contracted the disease have died.

Retroviruses were proposed as the causative agent of AIDS. Two such retroviruses now known to cause AIDS have been identified and isolated: LAV (lymphadenopathy-associated virus) and HTLV-III (human T-cell leukemia virus). It was later determined that LAV and HTLV-III are identical. Antibodies to these viruses are present in over 80% of patients diagnosed as having AIDS or pre-AIDS syndrome, and they have also been found with high frequency in the identified risk groups.

There is considerable difficulty in diagnosing the risk of development of AIDS. AIDS is known to develop in at least 10% of the individuals infected with HTLV-III/LAV, although this percentage is suspected to be higher.

A patient is generally diagnosed as having AIDS when a previously healthy adult with an intact immune system acquires impaired T-cell immunity. The impaired immunity usually appears over a period of 18 months to 3 years. As a result of this impaired immunity, the patient becomes susceptible to opportunistic infections, various types of cancer such as Kaposi's sarcoma, and other disorders associated with reduced functioning of the immune system.

Another condition associated with HTLV-III/LAV is AIDS-related complex, or ARC. This condition is thought to lead to AIDS in some cases.

No treatment capable of preventing the disease or reversing the immunodeficiency of AIDS or ARC is currently available. All patients with opportunistic infections and approximately half of all patients with Kaposi's sarcoma have died within two years of diagnosis. Attempts at reviving the immune systems in patients with AIDS have been unsuccessful.

Recently, it has been reported that 3'-azido-3'-deoxythymidine (AzT) is an antiviral agent that inhibits the infectivity and cytopathic effect of HTLV-III/LAV in vitro. See Mitsuya, et al, Proc. Natl. Acad. Sci. USA 82, 7096-100 (1985). However, preliminary results indicate that this compound exhibits toxicity in a clinical setting. See Yarchoan et al, Lancet 575-580 (1986). AzT was originally synthesized by Horwitz et al., J. Org. Chem. 29, 2076-2078, 1964. Its activity against Friend leukemia virus (a retrovirus) was reported as early as 1973 (see Ostertag et al, Proc. Natl. Acad. Sci. USA 71, 4980-4985 (1974) and Krieg et al, Exptl. Cell. Res. 116, 21-29, 1978 and references cited therein). The compounds of this invention are structurally quite similar to AzT, but are remarkably less toxic to normal cells and mice.

In general, inhibitors of cellular processes will often limit viral replication, but these agents are usually quite toxic for the host as well. Most of the antiviral drugs that have been discovered so far cannot be prescribed because of their toxicity. For example, a compound structurally related to the compounds of the present invention, idoxuridine, is limited in clinical usefulness to topical application in ophthalmic solutions for treatments of herpetic keratitis because of its toxicity to normal cells. Clearly, there is a strong demand for new antiviral agents of low toxicity.

Various other workers have disclosed compounds which are structurally similar to those of the present invention, some of which are reported to be antiviral agents. Lin et al., J. Med. Chem. 26, 1691-1696 (1983) and Lin et al., J. Med. Chem. 26, 544-548 (1983) each disclose the synthesis and biological activity of various 3'-azido and 3'-amino analogs of pyrimidine dideoxyribonucleosides. However, none of the present compounds were synthesized or disclosed in these references. Furthermore, no mention was made in this reference of use of the compounds to treat retroviruses such as HTLV-III/LAV.

Krenitsky et al., J. Med. Chem. 26, 891-895 (1983) discloses some 3'-amino-2',3'-dideoxyribonucleosides of some pyrimidines. However, none of these compounds have the particular $R_5$ substituents disclosed in the present invention. Furthermore, the HTLV-III/LAV is nowhere mentioned in this reference.

Some U.S. patents which disclose structurally related compounds, but which do not disclose any of the particular compounds of the present invention, include the following:

Eskstein, U.S. Pat. No. 4,331,662; Lin, U.S. Pat. No. 4,093,715; Greer, U.S. Pat. No. 4,210,638; Cook, U.S. Pat. No. 4,071,680; Verheyden I, U.S. Pat. No. 3,755,295; Bobek et al., U.S. Pat. No. 4,230,698; Lin et al., U.S. Pat. No. 4,128,639; Verheyden et al. II, U.S. Pat. No. 3,817,982; Verheyden et al. III, U.S. Pat. No. 3,687,931; Etzold, U.S. Pat. No. 3,775,397; and Verheyden IV, U.S. Pat. No. 3,282,921.

In view of the prior art, it is clear that there remains a strong need for new antiviral agents with low toxicity to normal cells. More particularly, because of the high mortality of AIDS and the lack of an effective treatment for this disease, there remains a great need for development of new low toxicity agents for such treatment. It was in this context that the present invention was achieved.

SUMMARY OF THE INVENTION

It is therefore an object of the present invention to provide new antiviral compounds having low toxicity towards uninfected cells.

It is a further object of this invention to provide compounds for inhibiting the growth of HTLV-III/LAV.

It is yet another object of the present invention to provide compositions for the treatment of individuals afflicted with AIDS or ARC.

Another object of this invention is to provide a method for the prevention and treatment of infection by HTLV-III/LAV.

These and other objects of the invention, which will hereinafter become more readily apparent, have been attained by providing compounds having the following formula:

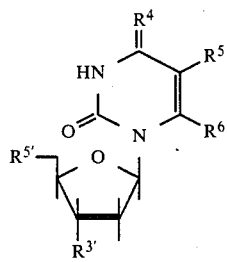

wherein $R^4$ is O or NH; $R^5$ is a $C_{2-4}$ alkyl group or a $C_{3-4}$ cycloalkyl group, which may be substituted by one or more of Cl, Br, I, F, OH, $N_3$, $NH_2$, $SO_3H$, or COOH; $R^6$ is hydrogen or a $C_{1-4}$ alkyl group, which may be substituted by Cl, Br, F, I, $N_3$, OH, $NH_2$, $SO_3H$, or COOH; $R^{3'}$ is $N_3$, $NH_2$, or H; and $R^{5'}$ is $N_3$, $NH_2$, OH, phosphate, or a $C_{1-4}$ acyl group. Also included within the scope of the invention are compositions including one or more of the above compounds. Further encompassed by the present invention is a method of prevention or treatment of AIDS or ARC, which involves administering a composition containing one or more of the above compounds to a person infected with HTLV-III/LAV or at risk of acquiring the virus.

BRIEF DESCRIPTION OF THE DRAWINGS

A more complete appreciation of the invention and many of the attendant advantages thereof will be readily obtained as the invention becomes better understood by reference to the following detailed description when considered in connection with the accompanying drawings, wherein.

DESCRIPTION OF THE PREFERRED EMBODIMENTS

Figure 1:
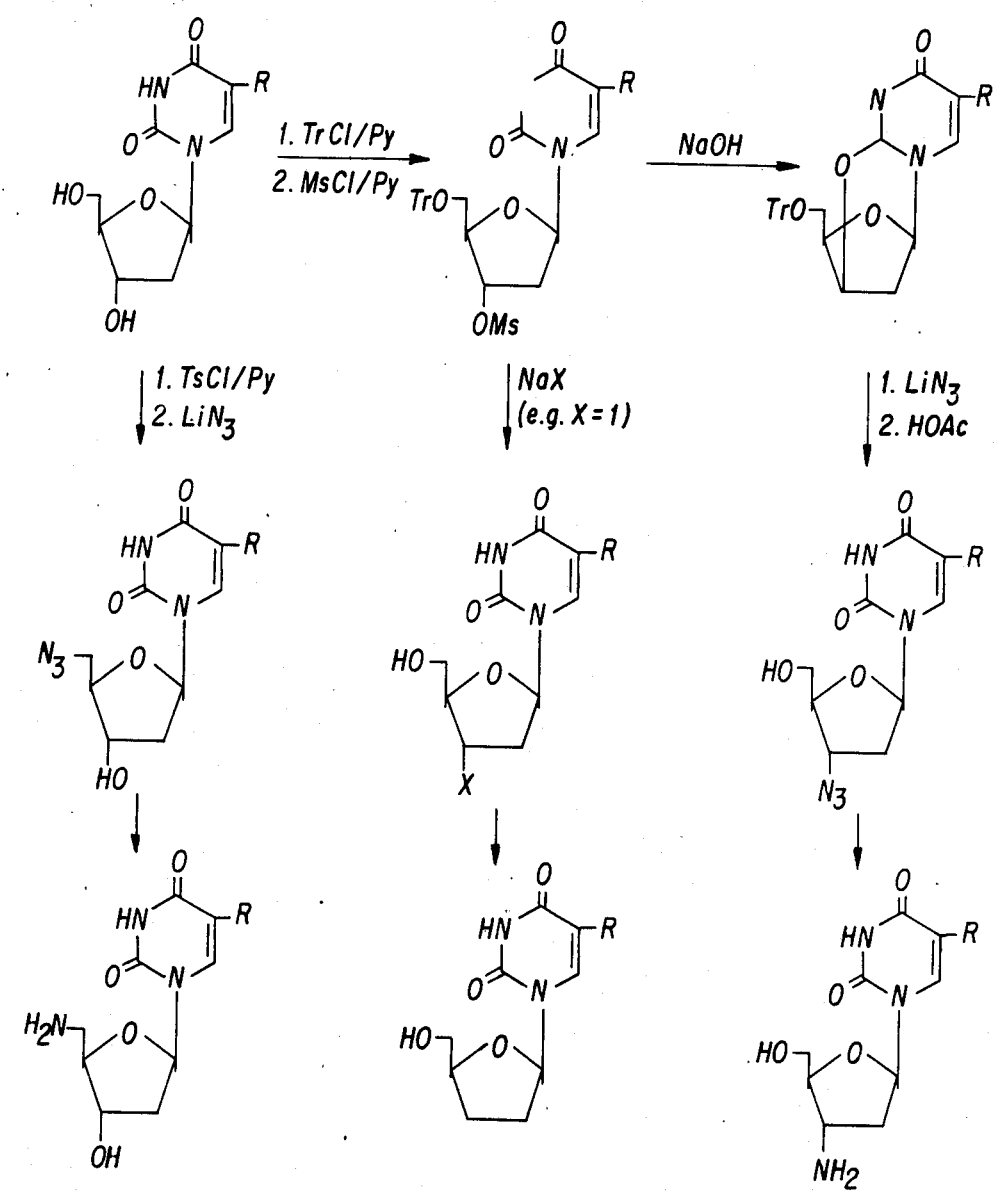
FIG. 1 is a scheme showing synthetic routes to compounds according to this invention. Specific examples of these steps may be found in the experimental examples.

The present invention is based on the discovery that certain 2',3'-dideoxy-5-substituted uridines and related compounds exhibit inhibitory activity towards viruses such as HTLV-III/LAV, yet at the same time exhibit very low toxicity towards normal cells. Following this discovery, it is now possible to treat viruses such as HTLV-III/LAV, in a manner which causes less damage to the host than with known anti-HTLV-III/LAV agents.

The discovery that the present compounds are active against HTLV-III/LAV and at the same time quite low in toxicity to normal host cells was surprising since a known compound of close structural similarity which is presently in clinical trials, 3'-azido-3'-deoxythymidine (AzT), exhibits a much greater toxicity as measured by various experiments. Both in vitro and in vivo testing results have shown that one of the present compounds in particular, 3'-azido-2',3'-dideoxy-5-ethyl-uridine (CS-85) is particularly effective in that it has almost equivalent activity to AzT but it is much lower in toxicity. Thus, CS-85 has a superior therapeutic index to AzT. The therapeutic index of a compound is determined by dividing the inhibitory or lethal dose for 50% of the population ($ID_{50}$ or $LD_{50}$) by the effective dose for 50% of the population ($ED_{50}$). The therapeutic index for AzT and CS-85 in cell culture was about 100 and $>2000$, respectively.

As used in this invention, antiviral activity refers to the ability of a compound to inhibit the growth of a virus. The virus of primary importance with respect to the present invention is HTLV-III/LAV. However, the present compounds may also exhibit antiviral activity towards other retroviruses. For example, CS-85 exhibits activity against murine retroviruses. The compounds may also have antibacterial properties.

The ability of a compound to inhibit HTLV-III/LAV may be measured by various experimental techniques. One such technique involves the inhibition of virus replication in human peripheral blood mononuclear cells. The amount of virus produced is determined by measuring the virus-coded reverse transcriptase (an enzyme found in retroviruses). Results with this assay are illustrated in the experimental examples below.

The compounds of this invention have the following structure:

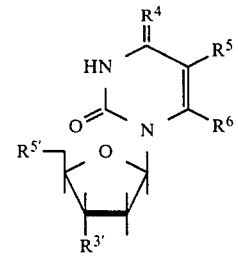

wherein $R^4$ is O or NH; $R^5$ is a $C_{2-4}$ alkyl group or a $C_{3-4}$ cycloalkyl group, wherein either the alkyl or cycloalkyl group which may be substituted by one or more of Cl, Br, I, F, OH, $N_3$, $NH_2$, $SO_3H$, or COOH; $R^6$ is hydrogen or a $C_{1-4}$ alkyl group, which may be substituted by Cl, Br, I, F, OH, $N_3$, $NH_2$, $SO_3H$, or COOH; $R^{3'}$ is $N_3$, $NH_2$, or H; and $R^{5'}$ is $N_3$, $NH_2$, OH, phosphate, or a $C_{1-4}$ acyl group.

The $C_{1-4}$ or $C_{2-4}$ alkyl groups of this invention may be, for example, methyl, ethyl, propyl, isopropyl, butyl, isobutyl, or tert-butyl. The $C_{3-4}$ cycloalkyl groups may be a cyclopropyl, methyl-cyclopropyl, or cyclobutyl group. Also encompassed by this invention are alkyl or cycloalkyl groups having one or more substitutents which may be, for example, halogens (Cl, Br, F, I), hydroxyl groups, azido and amino groups, sulphonic acid groups, or carboxylate groups. These substituents may be included on the alkyl or cycloalkyl groups to enhance the solubility of the compound in aqueous solution, or in other media. Preferably the present compounds have 0-2 of these substituents on the alkyl or cycloalkyl groups. When the compounds of the invention are substituted with amino groups or hydroxyl groups, these groups may be acylated with, for example, acetyl or propionyl groups. When the compounds of this invention are substituted with phosphate, sulphonate, or carboxylate groups, these groups may be in the protonated form, or may be any of various salts, such as, for example, potassium, sodium, and quaternary amine salts, etc. When amino groups are present on these compounds, they may be in the form of an acid addition salt such as the hydrochloride, acetate, hydrogensulfonate, etc.

Lyxo analogues of the present compounds are also encompassed within the scope of this invention. For example, the 3' substituents may have the opposite configuration from that shown in the FIGURE.

When $R^4$ is O, the compounds are uridine derivatives. When $R^4$ is NH, the compounds are cytidine derivatives.

A preferred group of compounds of this invention are those in which $R^4 = O$, $R^6 = H$, and $R^5$, $R^{3'}$ and $R^{5'}$ are as defined above.

A more preferred group of compounds of this invention are those in which $R^4 = O$, $R^5 = $ ethyl or ethyl substituted by any number of Cl, Br, I, F, $N_3$, OH, $NH_2$, $SO_3H$, or COOH.

A most preferred compound of this invention is 3'-azido-2',3'-dideoxy-5-ethyl-uridine (CS-85).

Specific compounds of this invention are the following:
3'-azido-2',3'-dideoxy-5-ethyl-uridine (CS-85),
3'-azido-2',3'-dideoxy-5-propyl-uridine,
3'-amino-2',3'-dideoxy-5-ethyl-uridine,
3'-amino-2',3'-dideoxy-5-propyl-uridine,
5'-azido-2',3',5'-trideoxy-5-ethyl-uridine,
5'-azido-2',3',5'-trideoxy-5-propyl-uridine,
5'-amino-2',3',5'-trideoxy-5-ethyl-uridine,
5'-amino-2',3',5'-trideoxy-5-propyl-uridine,
2',3'-dideoxy-5-ethyl-uridine (CS-86),
2',3'-dideoxy-5-propyl-uridine,
3'-azido-5'-amino-2',3',5'-trideoxy-5-ethyl-uridine,
3'-azido-5'-amino-2',3',5'-trideoxy-5-propyl-uridine,
5'-amino-3'-azido-2',3',5'-trideoxy-5-ethyl-uridine, and
5'-amino-3'-azido-2',3',5'-trideoxy-5-propyl-uridine.

Of course, this is just a small sampling of the compounds included within the scope of the present invention, and the invention is not limited thereto.

The compounds of this invention may be synthesized by methods known in the art. FIG. 1 depicts a general scheme which outlines the basic methods for synthesizing some of these compounds. Each of these reactions may be readily optimized for the particular substituent pattern by one of skill in the art based on prior art references. For example, Lin et al, J. Med. Chem. 26, 1691–1696 (1983) and Lin et al, J. Med. Chem. 26, 544–548 (1983) disclose various specific reactions which are similar to those outlined in FIG. 1. The choice of solvents, temperatures, and other reaction conditions may be readily ascertained without undue experimentation. Specific preparative examples of compounds falling within the scope of the present invention are provided in the experimental examples section below. The yield of the product depends on the column chromatography technique used.

Humans suffering from diseases caused by, for example, HTLV-III/LAV can be treated by administering to the patient a pharmaceutically effective amount of one or more of the present compounds optionally, but preferably in the presence of a pharmaceutically acceptable carrier or diluent. There may also be included pharmaceutically compatible binding agents, and/or adjuvant materials. The active materials can also be mixed with other active materials which do not impair the desired action and/or supplement the desired action. The active materials according to the present invention can be administered by any route, for example, orally, parenterally, intravenously, intradermally, subcutaneously, or topically, in liquid or solid form. For injection purposes, the medium used will be a sterile liquid. As an injection medium, it is preferred to use water which contains the stabilizing agents, solubilizing agents and/or buffers conventional in the case of injection solutions. Desirable additives include, for example, tartrate and borate buffers, ethanol, dimethylsulfoxide, complex forming agents (for example, ethylene diamine tetraacetic acid), high molecular weight polymers (for example, liquid polyethylene oxide) for viscosity regulation or polyethylene derivatives of sorbitan anhydrides.

Solid carrier materials include, for example, starch, lactose, mannitol, methyl cellulose, talc, high dispersed silicic acid, high molecular weight fatty acids (such as stearic acid), gelatin, agar-agar, calcium phosphate, magnesium stearate, animal and vegetable fats or solid high molecular weight polymers (such as polyethylene glycols). Compositions suitable for oral administration can, if desired, contain flavoring and/or sweetening agents.

A preferred mode of administration of the compounds of this invention is oral. Accordingly, the compounds may be formulated into capsule form.

The active materials according to the present invention can be employed in dosages and amounts which are conventional in the art. Thus, the materials can be used at a dosage range in humans of from 1 to 200 mg/kg total body weight/day. A more preferred range lies between 1 to 30 mg/kg total body weight/day. A most preferred range is 5 to 20 mg/kg total body weight/day. The dosages may be administered at once, or may be divided into a number of smaller doses to be administered at varying intervals of time.

The invention now being generally described, the same will be better understood by reference to certain specific examples which are included herein for purposes of illustration only and are not intended to be limiting of the invention or any embodiment thereof, unless specified.

EXPERIMENTAL EXAMPLES

Synthesis of compounds

Some exemplary syntheses of specific compounds of this invention are as follows.

EXAMPLE 1

5-Ethyl-5'-O-trityl-2'-deoxyuridine

To a solution of 5-ethyl-2'-deoxyuridine (4.0 g, 15.63 mmole) in dry pyridine (50 ml), trityl chloride (6.0 g, 21.5 mmole) is added at once and the mixture is heated at 100° C. for 1 hour. Thin-layer chromatography (tlc) shows the continued presence of the starting material. Additional amounts of trityl chloride (1.0 g) is added and the mixture is heated for another hour at the same temperature. After heating, the mixture is poured into an ice-water mixture (1 liter) while stirring. The resulting white precipitates are filtered for collection after successive washing with cold water. The precipitate is dissolved in chloroform and dried (over $MgSO_4$). The solvent is then evaporated to give a foam (7.5 g, 98%). This material is sufficiently pure to carry out the next reaction without further purification. However, an analytical sample can be obtained by column chromatography or tlc using a mixture of chloroform and methanol (20:1).

The product was pure enough for direct use in the next reaction.

EXAMPLE 2

5-Ethyl-3'-O-methanesulfonyl-5'-O-trityl-2'-deoxyuridine

To a solution of 5-ethyl-5'-O-trityl-2'-deoxyuridine (7.5 g, 15 mmole) in dry pyridine (50 ml), methanesulfonyl chloride (4.0 g, 35 mmole) is added while cooling in an ice-water bath. The mixture is stirred for one hour at around 0° C. and followed by allowing the temperature to rise to room temperature. At this point, tlc indicates no remaining starting materials. The mixture is then poured into an ice-water mixture (1.5 liters) while stirring, the water is decanted, and the product is washed with cold water several times, dissolved in chloroform and dried (over MgSO$_4$). Finally, the solvent is evacuated in vacuo to obtain a syrup (7.6 g, 90%). This material is sufficiently pure to carry out the next reaction without further purification. However, an analytical sample can be obtained by column chromatography or tlc using chloroform as an eluent.

Anal. Calc'd for $C_{30}H_{30}N_2O_5$: C, 66.43; H, 5.71; N, 5.00; S, 5.71.

Found: C, 64.46; H, 5.63; N, 4.80, S, 5.48.

EXAMPLE 3

2,3'-Anhydro-5-ethyl-5'-O-trityl-uridine

To a refluxing ethanolic solution of 5-ethyl-3'-O methanesulfonyl-5'-O-trityl-2'-deoxyuridine (5.76 g, 10 mmole) 1N NaOH (10 ml, 10 mmole) is added dropwise. Refluxing is continued for 15 minutes until tlc indicates no remaining starting materials. The solvent is then evacuated in vacuo to dryness. Water is added, and the product is triturated and filtered to collect a white amorphous precipitate (4.1 g). A pure sample (as a foam) can be obtained from a silica gel column using a chloroform-methanol (20:1) mixture as an eluent (1.8 g, 37%). m.p. 162°–168° C.

Anal. Calc'd for $C_{30}H_{31}N_2O_4 \cdot CH_3OH$: C, 72.66; H, 6.24; N, 5.47.

Found: C, 72.78; H, 5.78; N, 5.63.

EXAMPLE 4

3'-Azido-5-ethyl-5'-O-trityl-2',3'-dideoxyuridine

A mixture of 2,3'-anhydro-5-ethyl-5'-O-trityl uridine (10.0 g, 20 mmole) and sodium azide (5.0 g, 77 mmole) or lithium azide (3.0 g) in a mixture of DMF (100 ml) and water (7 ml) is refluxed for 15 hours, after which the solvents were removed by a mechanical pump and the resulting residue is dissolved in chloroform (60 ml), extracted with water (20 ml×2), dried (over MgSO$_4$), and filtered. The filtrate is evaporated to a syrup. A pure sample (as a foam) is obtained after passage through a silica gel column using chloroform-methanol (50:1) as an eluent (3.5 g, 32%). m.p. 68°–71° C.

Anal. Calc'd for $C_{30}H_{29}N_5O_4 \cdot CH_3OH$: C, 67.03; H, 5.95; N, 12.61.

Found: C, 67.08; H, 5.73; N, 13.32.

EXAMPLE 5

3'-Azido-2',3'-dideoxy-5-ethyl-uridine (CS-85)

A mixture of 3'-azido-5-ethyl-5'-O-trityl-2',3'-dideoxyuridine (0.9 g, 1.72 mmole) and 80% acetic acid (25 ml) is heated at 85°–90° C. for 40 minutes, after which acetic acid is evacuated in vacuo to a solid in which water (50 ml) is added, and the mixture is stirred for 10 minutes. The solution is filtered through a celite pad, and then the filtrate is extracted with n-hexane. The water layer is separated, evaporated down to ca. 2 ml, and then the solution is freeze-dried to yield an amorphous powder (400 mg, 83%). Recrystallization from MeOH gives fine needles. m.p. 118°–120° C.

Anal. Calc'd for $C_{11}H_{15}N_5O_4$: C, 46.98; H, 5.34; N, 24.91.

Found: C, 46.47; H, 5.33; N, 24.55.

EXAMPLE 6

3'-Amino-5-ethyl-2',3'-dideoxyuridine

An aqueous solution (15 ml) of 3'-azido-5-ethyl-2',3'-dideoxyuridine (376 mg) is hydrogenated with 10% Pd/C (100 mg) at room temperature under 1 atmosphere for one hour. The mixture is filtered through a celite pad, evaporated down to ca. 2 ml, and then freeze-dried to obtain a foam (300 mg, 88%).

Anal. Calc'd for $C_{11}H_{17}N_3O_4 \cdot \frac{1}{2}H_2O$: C, 50.00; H, 6.82; N, 15.90.

Found: C, 50.16; H, 6.95; N, 15.22.

EXAMPLE 7

5-Ethyl-5'-O-tosyl-2'-deoxyuridine

To an ice-cooled solution of 5-ethyl-2'-deoxyuridine (1.0 g, 3.9 mmole) in dry pyridine (10 ml), is added p-toluenesulfonyl chloride (0.83 g, 4.4 mmole) and the reaction is kept at 0° C. for 42 hours. Tlc indicates that the starting material remains. Additional p-toluenesulfonyl chloride (180 mg) is added, and the solution is stirred at ca. 0° C. for 5 hours. The mixture is then evacuated in vacuo to a syrup, which is chromatographed on a short vacuum silica gel column using chloroform-methanol (15:1) to yield a white amorphous powder (630 mg, 39%), m.p. 173°–175° C.

Anal. Calc'd for $C_{18}H_{22}N_2S_1O_7$: C, 52.68; H, 5.37; N, 6.83; S, 7.80.

Found: C, 52.43; H, 5.42; N, 6.78; S, 7.72.

EXAMPLE 8

5'-Azido-5-ethyl-2',5'-dideoxyuridine

A mixture of 5-ethyl-5'-O-tosyl-2'-deoxyuridine (550 mg, 1.34 mmole) and sodium azide (480 mg, 7.4 mmole) or lithium azide (400 mg) in dry dimethylformamide (10 ml) is heated at 85° C. for 2 hr. Tlc indicates all the starting material has reacted. The solvent is evaporated in vacuo to dryness, and the remaining material is triturated with ice-cold water, filtered to collect the product, and dried over P$_2$O$_5$ to give a white solid (340 mg, 90%), m.p. 174°–177° C.

Anal. Calc'd for $C_{11}H_{15}N_5O_4$: C, 46.98; H, 5.34; N, 24.91.

Found C, 46.91; H, 5.39; N, 26.81.

EXAMPLE 9

5'-Amino-5-ethyl-2',5'-dideoxyuridine

5'-Azido-5-ethyl-2',5'-dideoxyuridine (300 mg) is dissolved in a mixture of water-methanol (1:1, 25 ml) and then hydrogen gas is introduced with 10% Pd/C at room temperature under 1 atmosphere for 2 hr, after which the mixture is filtered and the filtrate is evaporated to a foam (160 mg, 50%).

Anal. Calc'd for $C_{11}H_{17}N_3O_4 \cdot \frac{1}{2}H_2O$: C, 50.50; H, 6.52; N, 15.90.

Found C, 49.72; H, 6.95; N, 15.44.

EXAMPLE 10

3'-Iodo-5-ethyl-5'-O-trityl-2',3'-dideoxyuridine

A mixture of 5-ethyl-3'-O-methanesulfonyl-5'-O-trityl-2'-deoxyuridine (3.2 g, 5.6 mmole) and sodium iodide (15.0 g, 100 mmole) in 1,2-dimethoxyethane is refluxed for 18 hr.

The mixture is cooled to room temperature, unreacted NaI is filtered, the solvent is evaporated, and the remaining material is redissolved in $CH_2Cl_2$. The remaining inorganic salt (NaI) is extracted with water, and the brown solution is washed with 5% sodium thiosulfate solution. The organic layer is separated, dried (over $MgSO_4$), and filtered. The filtrate is evaporated to a syrup, which is chromatographed on a silica gel column using chloroform-methanol (70:1) initially followed by chloroform-methanol (50:1), to obtain a white foam (1.98 g, 59%).

Anal Calc'd for $C_{30}H_{29}N_2IO_4$: C, 59.21; H, 4.77; N, 4.61; I, 20.89.

Found: C, 59.28; H, 4.82; N, 4.56; I, 20.92.

EXAMPLE 11

5-Ethyl-3'-iodo-2',3'-dideoxyuridine

A mixture of 5-ethyl-3'-Iodo-5'-O-trityl-2',3'-dideoxyuridine (1.73 g, 2.8 mmole) and 80% HAc (25 ml) is heated at 100° C. for 50 min. After heating, acetic acid is evacuated in vacuo to obtain an amorphous solid. Ether is added, the product is triturated, and the resulting yellowish solid is filtered for collection (350 mg). Another 250 mg is obtained from the filtrate after repeating the above procedure, m.p. 162°–164° C.

Anal. calc'd for $C_{11}H_5N_2IO_4$: C, 36.07; H, 4.10; N, 7.65; I, 34.70.

Found: C, 36.03; H, 4.11; N, 7.62; I, 34.57.

EXAMPLE 12

5-Ethyl-2',3'-dideoxyuridine (CS-86)

5-Ethyl-3'-iodo-2',3'-dideoxyuridine (432 mg, 0.87 mmole) is dissolved in methanol (40 ml) and triethylamine (0.5 ml) is added along with 10% Pd/C (200 mg). The mixture is then stirred in an atmosphere of hydrogen at room temperature for 30 min. After filtration of catalyst, the filtrate is evaporated to dryness. Purification of the product was achieved on silica gel plates using chloroform-methanol (20:1) to obtain a solid (150 mg, 75%).

Anal. calc'd for $C_{11}H_{16}N_2O_4$: C, 55.00; H, 6.68; N, 11.67.

Found: C, 54.95; H, 6.49; N, 11.85.

EXAMPLE 13

3'-Azido-2',3'-dideoxy-5-Propyl-uridine

A mixture of 5-propyl-2'-deoxyuridine (5.53 g, 20 mmole), trityl chloride (6.14 g, 22 mmole) and pyridine (50 ml) is heated at 100° C. for two hours. The mixture is then poured into an ice-water mixture. The supernatant is decanted and the resulting syrup is dissolved in chloroform, dried (over $MgSO_4$), and the evaporation of the solvent gives a syrup. The syrup is dissolved in pyridine (35 ml) and cooled in an ice-water bath in which methanesulfonyl chloride (5.0 g) is added. The mixture is stirred at ca.0° C. for two hours, after which it is poured into an ice-water mixture. The supernatant is decanted, and the remaining crude product is dissolved in chloroform, dried (over $MgSO_4$), and then evaporated to a syrup, which is used for the next step.

The syrup is heated to reflux in ethanol (3 ml) and then 1 N NaOH is added dropwise until the starting material disappears (about 10.5 ml) as determined by TLC. The mixture is evaporated to a syrup, which is chromatographed on silica gel using methanol-chloroform (1:35) to obtain a pure product (1.16 g) and less pure product (2.0 g). The pure product (1.16 g) is treated with $LiN_3$ (1.0 g) at 95°–100° C. in DMF for 15 hours, after which the solvent is evacuated to obtain a syrup, which is purified by a silica gel column using chloroform-methanol (30:1) to give 0.75 g of 3'-azido-5-propyl-5'-O-trityl-2',3'-dideoxyuridine.

A mixture of the above compound (640 mg) and 80% HAc (15 ml) is heated at 90°–95° C. for one hour. The mixture is evaporated to a syrup, to which water was added. The product is triturated, filtered, and the filtrate is evaporated to a syrup (180 mg).

Anal. calc'd for $C_{12}H_{18}N_5O_5 \cdot 0.5H_2O$: C, 47.37; H, 5.92; N, 23.03.

Found: C, 47.62; H, 5.74; N, 23.14.

BIOLOGICAL DATA

Antiviral Assay 1. 4–7 day-old PHA-stimulated human peripheral blood mononuclear cells from healthy volunteers ($1 \times 10^6$ cells per ml; volume=5 ml) are placed in a 25 $cm^2$ flask.

2. The medium, with ($2 \times$ the final concentration) or without drug, is added to the flasks (5 ml; final volume=10 ml).

3. The flasks are then infected with about 5,000 cpm reverse transcriptase (RT)/ml or 50,000 cpm RT/flask and are then placed in a $CO_2$ incubator. LAV was obtained from the Centers for Disease Control, Atlanta. The RT levels of the stock virus is usually 0.8 to 1.3 million cpm RT/ml.

4. The next day (day 1), the supernatant is removed and the cells are replenished with fresh medium with or without drug ($1 \times$ the final concentration). This step is optional.

5. On day 5, cells and supernatant are transferred to a 15 ml tube and centrifuged at about 900 rpm for 10 minutes. Four ml (or more if desired) of supernatant are removed and processed for determination of reverse transcriptase activity. The rest of the supernatant is discarded.

6. The cells are resuspended in fresh medium without drugs and replaced in the original flask.

7. The flasks are then incubated for one week, and on day 12 after infection, step 5 is repeated (to measure virus breakthrough).

Using the RT assay, the results shown in Table 1 were obtained.

TABLE 1

Effect of several 3'-substituted pyrimidine nucleosides on the replication of HTLV-III/LAV in human peripheral blood mononuclear cells (Reverse transcriptase assay of supernatants) as described above.

| Compound | Conc., μM | C.P.M./ml DAY 5 | Cor. % inhib. DAY 5 | C.P.M./ml DAY 12[a] | Cor. % inhib. DAY 12[a] |
|---|---|---|---|---|---|
| Virus control | — | 840,640 | | 363,580 | |
| AzT | 0.1 | 5,320 | 99.65 | 4,565 | 99.26 |
| | 1 | 3,660 | 99.84 | 5,340 | 99.05 |
| | 10 | 3,430 | 99.87 | 4,990 | 99.15 |
| | 100 | 1,980 | 100.04 | 3,755 | 99.49 |
| CS-85 | 0.1 | 4,205 | 99.78 | 10,590 | 97.61 |
| | 1 | ND | ND | 5,515 | 99.00 |
| | 10 | 2,465 | 99.99 | 5,280 | 99.07 |
| | 100 | 1,370 | 100.12 | 9,380 | 97.94 |
| 3'-Amino-EdU[b] | 0.1 | ND | ND | 132,600 | 64.05 |
| | 1 | 59,980 | 93.14 | 46,980 | 87.60 |
| | 10 | 23,745 | 97.45 | 23,085 | 94.17 |
| | 100 | 23,910 | 97.43 | 23,560 | 94.04 |
| Cell Control (uninfected) | | 2,340 | 0 | 1,890 | 0 |
| Blank | | | | 1,195 | |
| Standard (control for RT assay) | | | | 888,380 | |

[a] On day 5, antiviral drug is removed and the cells are replenished with medium without the compounds. The RT levels in supernatants are redetermined on day 12.
[b] 3'-Amino-2',3'-dideoxy-5-ethyl-uridine.

This experiment shows that the CS-85 has significant activity in inhibiting replication of HTLV-III/LAV in vitro (Table 1). 3'-Amino-5-deoxy-ethyl-uridine is somewhat less active than either CS-85 or AzT.

When the cells are infected with less virus and the drug is added after virus infection, AzT is somewhat more active than CS-85. 2',3'-dideoxy-5-ethyl-uridine (CS-86) was less active than CS-85 in this assay.

A second experiment was conducted to show the effects of various compounds on replication of Vero and human foreskin fibroblasts (see Table 2). These cells, particularly the Vero cells, are very fast growing cells, and it can be seen that both CS-85 and 3'-amino deoxy-5-ethyl-uridine exhibit very little inhibition of these cells. This is indicative of much lower toxicity than AzT or 3'-amino-T, both of which inhibit a much higher percentage of these cells at a given concentration.

TABLE 2

Effect of 3-amino and azido substituted thymidine and 5-ethyl-2'-deoxyuridine on the replication of Vero and human foreskin fibroblasts.

| Compound | Concn, μM. | Vero cells % Inhibited[a] | Human Fibroblasts % Inhibited[a] |
|---|---|---|---|
| AzT | 10 | 21.0 | 41.5 |
| | 100 | 86.0 | 26.8 |
| | 500 | 92.6 | 61.0 |
| | 1000 | 89.7 | 36.6 |
| | 2000 | 88.2 | 46.3 |
| CS-85 | 10 | 0.0 | 0.0 |
| | 100 | 0.0 | 26.8 |
| | 500 | 0.0 | 7.3 |
| | 1000 | −2.6 | 19.5 |
| | 2000 | 53.5 | 17.1 |
| 3'-Amino-EdU | 10 | 0.0 | 0.0 |
| | 100 | 0.0 | 0.0 |
| | 500 | 6.3 | −9.8 |
| | 1000 | 23.2 | 17.1 |
| | 2000 | 32.8 | −7.3 |
| 3'-Amino-T[b] | 1 | 24.0 | ND |
| | 10 | 43.9 | 46.3 |
| | 100 | 63.8 | 65.9 |
| | 200 | 74.9 | 61.0 |
| | 400 | 76.4 | 46.3 |

[a] On day 3, there were 1.02 × 10[6] and 1.54 × 10[5] Vero and HF cells, respectively, in the untreated control group. (For methods, see Schinazi et al, Antimicrob. Agents Chemother. 22, 499–507, 1982).

In a third experiment, it was found that as the amount of AzT is increased, the percentage inhibition of DNA synthesis increases dramatically (Table 3). AT a concentration of 200 μM of AzT, 91.4% of the DNA synthesis is inhibited as compared to a control experiment. Similar results are obtained when labeled 2'-deoxycytidine is used instead of thymidine. Unexpectedly, in the case of CS-85, the amount of DNA synthesis inhibition actually goes down as the concentration of CS-85 increases, up to a level of 400 μM. At higher concentrations of CS-85 the percentage of inhibition of DNA synthesis begins to increase. It is particularly surprising to note that CS-85 and AzT exhibit opposite trends as the concentration is increased up to 400 μM. At 400 μM CS-85, the degree of inhibition of DNA synthesis is negligible.

TABLE 3

Effect of CS-85 and AzT on the synthesis of DNA in uninfected human blood peripheral mononuclear (PBM) cells.

| Sample | Compound | Concn. μM | CPM | CPM | Average CPM | % of Control |
|---|---|---|---|---|---|---|
| 1 | None | 0 | 2970 | 2884 | 2927.0 | 100.0 |
| 2 | AzT | 1 | 1690 | 1671 | 1680.5 | 57.4 |
| 3 | | 10 | 1360 | 1396 | 1378.0 | 47.1 |
| 4 | | 100 | 301 | 292 | 296.5 | 10.1 |
| 5 | | 200 | 249 | 255 | 252.0 | 8.6 |
| 7 | CS-85 | 1 | 2322 | 2310 | 2316.0 | 79.1 |
| 8 | | 10 | 2330 | 2281 | 2305.5 | 78.8 |
| 9 | | 100 | 2535 | 2532 | 2533.5 | 86.6 |
| 10 | | 200 | 2574 | 2551 | 2562.5 | 87.5 |
| 11 | | 400 | 2933 | 2915 | 2924.0 | 99.9 |
| 12 | | 800 | 2049 | 2028 | 2038.5 | 69.6 |

TABLE 3-continued

Effect of CS-85 and AzT on the synthesis of DNA in uninfected human blood peripheral mononuclear (PBM) cells.

| Sample | Compound | Concn. μM | CPM | CPM | Average CPM | % of Control |
|---|---|---|---|---|---|---|
| 13 | | 1600 | 1493 | 1543 | 1518.0 | 51.9 |

[a]PMB cells (10[7]) were exposed to the antiviral drugs or medium at 37° C. for 24 h in a $CO_2$ incubator. The cells were then pulsed with about 1 μCi[³H]thymidine for 105 min. At the end of the pulse, the cells wereharvested on glass fiber filters, washed with 5% TCA (5×), and then with 70% EtOH (3×). After drying, the filters were counted in econofluor scintillation fluid in a liquid scintillation counter.

In a fourth experiment, it was found that the $ID_{50}$ of CS-85 is approximately 25 to 17 fold higher than that for AzT to human bone marrow precursor cells (Table 4). It is 10 fold higher than that for DHPG. Similarly, the $ID_{90}$ is much higher for CS-85 than either AzT or DHPG. This is clearly suggestive of a lower toxic effect on human bone marrow cells.

Figure 2:
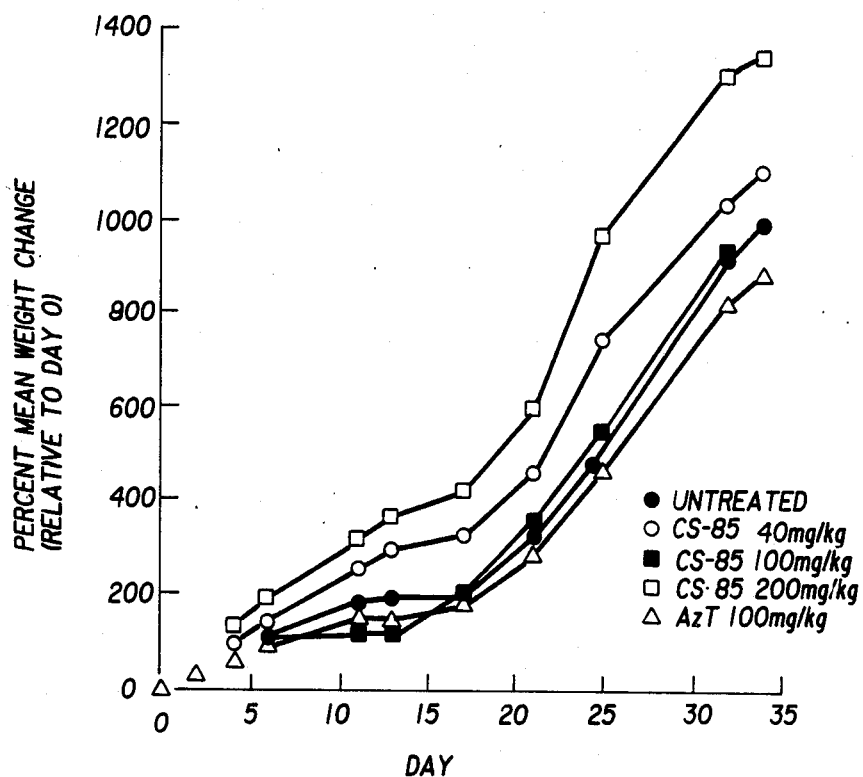
FIG. 2 is a graph showing the effect of 3'-azido-2',3'-dideoxy-5-ethyluridine (CS-85) and 3'-azido-3'-deoxythymidine (AzT) on the growth of newborn outbred Swiss mice (2-4 days old at the time of treatment).

CS-85 was tested in newborn mice (2-4 days old) to determine if it causes mortality or loss in weight. Up to 200 mg/kg per day for 7 days caused no adverse effects with this drug (see FIG. 2).

TABLE 4

Effect of CS-85, AzT, and DHPG on the replication of human monocyte and granulocyte precursor cells.[a]

| Compound | $ID_{50}$, μM[b] | $ID_{90}$, μM |
|---|---|---|
| CS-85 | ca. 50 | 500 |
| AzT | 2-3 | 20-25 |
| DHPG[c] | 5 | 25 |

[a]Cells were continuously exposed to the drugs for 14 days.
[b]$ID_{50}$ is the median inhibitory dose.
[c]Dihydropropoxy-methylguanosine.

The invention now being fully described, it will be apparent to one of ordinary skill in the art that many changes and modifications can be made thereto without departing from the spirit or scope of the invention as set forth herein.

What is claimed as new and desired to be secured by Letters Patent of the United States is:

1. The compound which is 3'-azido-2',3'-dideoxy-5-ethyl-uridine.
2. The compound which is 3'-azido-2',3'-dideoxy-5-propyl-uridine.
3. The compound which is 5'-azido-2',3',5'-trideoxy-5-ethyl-uridine.
4. The compound which is 5'-azido-2',3',5'-trideoxy-5-propyl-uridine.
5. The compound which is 3'-azido-5'-amino-2',3',5'-trideoxy-5-ethyl-uridine.
6. The compound which is 3'-azido-5'-amino-2',3',5'-trideoxy-5-propyl-uridine.

* * * * *